(12) United States Patent
Farascioni

(10) Patent No.: US 8,906,036 B2
(45) Date of Patent: Dec. 9, 2014

(54) SURGICAL RETRIEVAL APPARATUS

(71) Applicant: Covidien LP, Mansfield, MA (US)

(72) Inventor: David M. Farascioni, Bethel, CT (US)

(73) Assignee: Covidien LP, Mansfield, MA (US)

( * ) Notice: Subject to any disclaimer, the term of this patent is extended or adjusted under 35 U.S.C. 154(b) by 244 days.

(21) Appl. No.: 13/668,342

(22) Filed: Nov. 5, 2012

(65) Prior Publication Data

US 2013/0131689 A1 May 23, 2013

Related U.S. Application Data

(60) Provisional application No. 61/562,097, filed on Nov. 21, 2011.

(51) Int. Cl.
*A61B 17/24* (2006.01)
*A61B 17/00* (2006.01)

(52) U.S. Cl.
CPC . *A61B 17/00234* (2013.01); *A61B 2017/00287* (2013.01)
USPC .......................................................... 606/114

(58) Field of Classification Search
USPC .............. 383/33, 37, 38, 71, 72, 75; 600/582; 604/163; 606/110, 113, 114, 115, 127, 606/128; 128/842, 844, 885
See application file for complete search history.

(56) References Cited

U.S. PATENT DOCUMENTS

| | | | |
|---|---|---|---|
| 30,471 A | 10/1860 | Dudley | |
| 35,164 A | 5/1862 | Logan et al. | |
| 156,477 A | 11/1874 | Bradford | |
| 1,609,014 A | 11/1926 | Dowd | |
| 3,800,781 A | 4/1974 | Zalucki | |
| 3,977,450 A * | 8/1976 | Schampier | 383/7 |
| 4,146,133 A * | 3/1979 | Bogorad et al. | 206/439 |
| 4,312,473 A * | 1/1982 | Hoeller | 383/38 |
| 4,428,484 A * | 1/1984 | Rattay et al. | 206/548 |
| 4,557,255 A | 12/1985 | Goodman | |
| 4,611,594 A | 9/1986 | Grayhack et al. | |
| 4,744,363 A | 5/1988 | Hasson | |

(Continued)

FOREIGN PATENT DOCUMENTS

DE 3542667 A1 6/1986
DE 8435489 U1 8/1986

(Continued)

OTHER PUBLICATIONS

European Search Report EP 12 15 0271 dated Jan. 14, 2013.

(Continued)

*Primary Examiner* — Ryan Severson
*Assistant Examiner* — Jonathan W Miles

(57) ABSTRACT

A surgical retrieval apparatus for receipt of multiple tissue specimens includes a collection bag, a support ring, and a flip ring. The collection bag includes first and second packets each having an outer portion and an inner portion. The first and second packets define first and second adjacent chambers, respectively, that are each configured for receipt of a tissue specimen therein. The first and second packets are coupled to both the support ring and the flip ring. The flip ring is pivotably coupled to the support ring and is rotatable relative to the support ring between a first position, wherein the first chamber is accessible for depositing a tissue specimen therein and a second position, wherein the second chamber is accessible for depositing a tissue specimen therein.

16 Claims, 4 Drawing Sheets

(56) References Cited

U.S. PATENT DOCUMENTS

| | | | |
|---|---|---|---|
| 4,750,639 A * | 6/1988 | Schaerer | 383/37 |
| 4,790,812 A | 12/1988 | Hawkins, Jr. et al. | |
| 4,927,427 A | 5/1990 | Kriauciunas et al. | |
| 4,997,435 A | 3/1991 | Demeter | |
| 5,018,876 A * | 5/1991 | Mennella | 383/1 |
| 5,037,379 A | 8/1991 | Clayman et al. | |
| 5,050,998 A * | 9/1991 | Wachtel | 383/6 |
| 5,074,867 A | 12/1991 | Wilk | |
| 5,084,054 A | 1/1992 | Bencini et al. | |
| 5,143,082 A | 9/1992 | Kindberg et al. | |
| 5,147,371 A | 9/1992 | Washington et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,190,561 A | 3/1993 | Graber | |
| 5,192,284 A | 3/1993 | Pleatman | |
| 5,192,286 A | 3/1993 | Phan et al. | |
| 5,201,740 A | 4/1993 | Nakao et al. | |
| 5,215,521 A | 6/1993 | Cochran et al. | |
| 5,234,439 A | 8/1993 | Wilk et al. | |
| 5,279,539 A | 1/1994 | Bohan et al. | |
| 5,312,416 A | 5/1994 | Spaeth et al. | |
| 5,330,483 A | 7/1994 | Heaven et al. | |
| 5,336,227 A | 8/1994 | Nakao et al. | |
| 5,337,754 A | 8/1994 | Heaven et al. | |
| 5,341,815 A | 8/1994 | Cofone et al. | |
| 5,352,184 A | 10/1994 | Goldberg et al. | |
| 5,354,303 A | 10/1994 | Spaeth et al. | |
| 5,368,545 A | 11/1994 | Schaller et al. | |
| 5,368,597 A | 11/1994 | Pagedas | |
| 5,370,647 A | 12/1994 | Graber et al. | |
| 5,443,472 A | 8/1995 | Li | |
| 5,465,731 A | 11/1995 | Bell et al. | |
| 5,480,404 A | 1/1996 | Kammerer et al. | |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,630,822 A | 5/1997 | Hermann et al. | |
| 5,643,282 A | 7/1997 | Kieturakis | |
| 5,643,283 A | 7/1997 | Younker | |
| 5,645,083 A | 7/1997 | Essig et al. | |
| 5,647,372 A | 7/1997 | Tovey et al. | |
| 5,649,902 A | 7/1997 | Yoon | |
| 5,658,296 A | 8/1997 | Bates et al. | |
| 5,679,423 A | 10/1997 | Shah | |
| 5,735,289 A | 4/1998 | Pfeffer et al. | |
| 5,755,724 A | 5/1998 | Yoon | |
| 5,759,187 A | 6/1998 | Nakao et al. | |
| 5,769,794 A | 6/1998 | Conlan et al. | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,836,953 A | 11/1998 | Yoon | |
| 5,853,374 A | 12/1998 | Hart et al. | |
| 5,895,392 A | 4/1999 | Riek et al. | |
| 5,906,621 A | 5/1999 | Secrest et al. | |
| 5,957,884 A | 9/1999 | Hooven | |
| 5,971,995 A | 10/1999 | Rousseau | |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,019,770 A | 2/2000 | Christoudias | |
| 6,036,363 A * | 3/2000 | Behnk | 383/38 |
| 6,036,681 A | 3/2000 | Hooven | |
| 6,059,793 A | 5/2000 | Pagedas | |
| 6,123,701 A | 9/2000 | Nezhat | |
| 6,152,932 A | 11/2000 | Ternstrom | |
| 6,162,235 A | 12/2000 | Vaitekunas | |
| 6,165,121 A | 12/2000 | Alferness | |
| 6,168,603 B1 | 1/2001 | Leslie et al. | |
| 6,228,095 B1 | 5/2001 | Dennis | |
| 6,234,675 B1 * | 5/2001 | Saad et al. | 383/38 |
| 6,270,505 B1 | 8/2001 | Yoshida et al. | |
| 6,277,083 B1 | 8/2001 | Eggers et al. | |
| 6,280,450 B1 | 8/2001 | McGuckin, Jr. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 | 2/2002 | Stefanchik | |
| 6,383,195 B1 | 5/2002 | Richard | |
| 6,383,196 B1 | 5/2002 | Leslie et al. | |
| 6,383,197 B1 | 5/2002 | Conlon et al. | |
| 6,406,440 B1 | 6/2002 | Stefanchik | |
| 6,409,733 B1 | 6/2002 | Conlon et al. | |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,537,273 B1 | 3/2003 | Sosiak et al. | |
| 6,589,252 B2 | 7/2003 | McGuckin, Jr. | |
| 6,752,811 B2 | 6/2004 | Chu et al. | |
| 6,755,779 B2 | 6/2004 | Vanden Hoek et al. | |
| 6,780,193 B2 | 8/2004 | Leslie et al. | |
| 6,805,699 B2 | 10/2004 | Shimm | |
| 6,840,948 B2 | 1/2005 | Albrecht et al. | |
| 6,872,211 B2 | 3/2005 | White et al. | |
| 6,887,255 B2 | 5/2005 | Shimm | |
| 6,994,696 B2 | 2/2006 | Suga | |
| 7,052,454 B2 | 5/2006 | Taylor | |
| 7,052,501 B2 | 5/2006 | McGuckin, Jr. | |
| 7,090,637 B2 | 8/2006 | Danitz et al. | |
| 7,219,814 B2 * | 5/2007 | Lown et al. | 220/739 |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,547,310 B2 | 6/2009 | Whitfield | |
| 7,670,346 B2 * | 3/2010 | Whitfield | 606/114 |
| 7,837,612 B2 | 11/2010 | Gill et al. | |
| 2003/0100919 A1 | 5/2003 | Hopkins et al. | |
| 2004/0097960 A1 | 5/2004 | Terachi et al. | |
| 2004/0138587 A1 | 7/2004 | Lyons | |
| 2005/0084182 A1 * | 4/2005 | Penson | 383/38 |
| 2005/0267492 A1 | 12/2005 | Poncet et al. | |
| 2006/0052799 A1 | 3/2006 | Middleman et al. | |
| 2006/0058776 A1 | 3/2006 | Bilsbury | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2007/0175787 A1 * | 8/2007 | Lown et al. | 206/427 |
| 2007/0223842 A1 * | 9/2007 | Sabounjian | 383/2 |
| 2008/0188766 A1 | 8/2008 | Gertner | |
| 2008/0221588 A1 | 9/2008 | Hollis et al. | |
| 2008/0234696 A1 | 9/2008 | Taylor et al. | |
| 2008/0300621 A1 | 12/2008 | Hopkins et al. | |
| 2008/0312496 A1 | 12/2008 | Zwolinski | |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |

FOREIGN PATENT DOCUMENTS

| | | |
|---|---|---|
| EP | 1707126 A1 | 10/2006 |
| EP | 2184014 A2 | 5/2010 |
| FR | 1272412 A | 9/1961 |
| WO | 9315675 A1 | 8/1993 |
| WO | 9509666 A1 | 4/1995 |
| WO | 2004002334 A1 | 1/2004 |

(56) References Cited

FOREIGN PATENT DOCUMENTS

| | | |
|---|---|---|
| WO | 2005112783 A1 | 12/2005 |
| WO | 2007/048078 A1 | 4/2007 |
| WO | 2009/149146 A1 | 12/2009 |

OTHER PUBLICATIONS

European Search Report 12 19 3450 dated Feb. 27, 2013.

\* cited by examiner

SURGICAL RETRIEVAL APPARATUS

CROSS-REFERENCE TO RELATED APPLICATIONS

This application claims the benefit of, and priority to, U.S. Provisional Patent Application No. 61/562,097, filed on Nov. 21, 2011, the entire contents of which are incorporated by reference herein.

BACKGROUND

1. Technical Field

The present disclosure relates to a retrieval apparatus, and more particularly, to surgical retrieval apparatus for removing tissue specimens from an internal body cavity.

2. Background of Related Art

In minimally-invasive surgical procedures, operations are carried out within the body by elongated instruments inserted through small entrance openings in the body. The entrance openings in the body tissue that allow passage of instruments to the interior of the body may be natural passageways of the body, may be created by a tissue piercing instrument, e.g., a trocar, or may be created by a small incision into which a cannula is inserted.

Because the tubes, instrumentation, and any required punctures or incisions are relatively small, minimally-invasive surgery is less invasive as compared to conventional open surgical procedures in which the surgeon is required to cut open large areas of body tissue. Therefore, minimally-invasive surgery minimizes trauma to the patient and reduces patient recovery time and hospital costs.

Minimally-invasive procedures may be used for partial or total removal of body tissue or organs from the interior of the body, e.g. nephrectomy, cholecystectomy, lobectomy, and other procedures including thoracic, laparoscopic, and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to inhibit seeding of cancer cells.

In minimally-invasive thoracic surgery, for example, access to the thoracic cavity as well as maneuverability within the thoracic cavity is limited since the access port is typically positioned within the confined space between a patient's ribs. Such procedures, commonly referred to as video assisted thorascopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thoracoscopic wedge resection and lobectomy, it is often necessary to remove a portion of the lung and retrieve it relatively intact for pathology. It is also important that the specimen be sufficiently contained to inhibit seeding of cancer cells during manipulation and removal.

In designing a surgical retrieval apparatus, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation should be designed to minimize the risk of seeding and be able to be inserted through a small access incision or port while also being capable of accommodating a wide range of patient sizes and specimen sizes.

SUMMARY

In accordance with the present disclosure, a surgical retrieval apparatus for receipt of multiple tissue specimens is provided. The surgical retrieval apparatus generally includes a collection bag, a support ring, and a flip ring. The collection bag includes first and second packets each having an outer portion and an inner portion. The first and second packets define first and second adjacent chambers that are each configured for receipt of a tissue specimen therein. The first and second packets are coupled to both the support ring and the flip ring. The flip ring is pivotably coupled to the support ring and is rotatable relative to the support ring between a first position, wherein the first chamber is accessible for depositing a tissue specimen therein, and a second position, wherein the second chamber is accessible for depositing a tissue specimen therein.

In embodiments, when the first chamber is accessible the second chamber is closed, and when the second chamber is accessible the first chamber is closed.

In embodiments, the outer portions of the first and second packets are engaged to the support ring. Additionally or alternatively, the inner portions of the first and second packets may be engaged to the flip ring.

The surgical retrieval apparatus, in embodiments, further includes an elongated tubular member and a rod rotatably disposed within the elongated tubular member. The elongated tubular member is coupled to the support ring and the rod is coupled to the flip ring such that rotation of the rod relative to the elongated tubular member rotates the flip ring between the first and second positions. A rotation knob may be coupled to the rod to effect corresponding rotation of the rod.

In embodiments, the collection bag is articulatable relative to the longitudinal axis of the elongated member. An articulation knob may be provided that is selectively movable to articulate the collection bag.

In embodiments, the inner portions of the first and second packets are attached to one another.

First and second sutures may be provided to extend between the first and second packets to facilitate cinching the first and second packets closed.

In embodiments, the support ring defines a generally circular configuration and/or the flip ring defines a generally semi-circular configuration.

In accordance with the present disclosure, another surgical retrieval apparatus is provided including a handle portion, an elongated tubular member, a collection bag, and a flip ring. The collection bag is positioned distal of the elongated tubular member and includes first and second packets. The first packet defines a first chamber with a first opening and the second packet defines a second chamber with a second opening. The flip ring is operably coupled to the collection bag and is movable between first and second positions to alternatingly expose the first and second openings of the first and second chambers, respectively.

In embodiments, a first suture is positioned about an open end of the first packet to cinch the first packet closed to retain a first specimen of tissue therein and/or a second suture is positioned about an open end of the second packet to cinch the second packet closed to retain a second specimen of tissue therein.

In embodiments, one or both of the first and second packets is releasable from the flip ring.

In embodiments, the flip ring is rotated via rotation of a rotation knob to alternatingly expose the first and second openings of the respective first and second chambers.

In accordance with the present disclosure, a method of manufacturing a multi-chamber collection bag for use in a surgical retrieval apparatus is provided. The method includes providing a sleeve of material having first and second open ends; forming a divider between the first and second open ends to divide the sleeve into first and second packets, each defining a chamber and having a closed end adjacent the divider and an open end; and attaching the packets to one another such that the chambers are positioned adjacent one another.

In embodiments, the divider is an RF weld formed in the sleeve.

The divider may be centrally formed between the first and second open ends such that the first and second chambers are substantially equal in size. Alternatively, the divider may be formed closer to one of the first and second open ends such that the first and second chambers define different sizes.

In embodiments, the method further includes coupling the first and second packets to a support ring. The method may additionally include coupling the first and second packets to a flip ring that is pivotably coupled to the support ring such that the flip ring may be rotated relative to the support ring to alternatingly provide access to the first and second chambers.

BRIEF DESCRIPTION OF THE DRAWINGS

Various embodiments of the subject surgical retrieval apparatus are described herein with reference to the drawings wherein.

DETAILED DESCRIPTION

Figure 1:
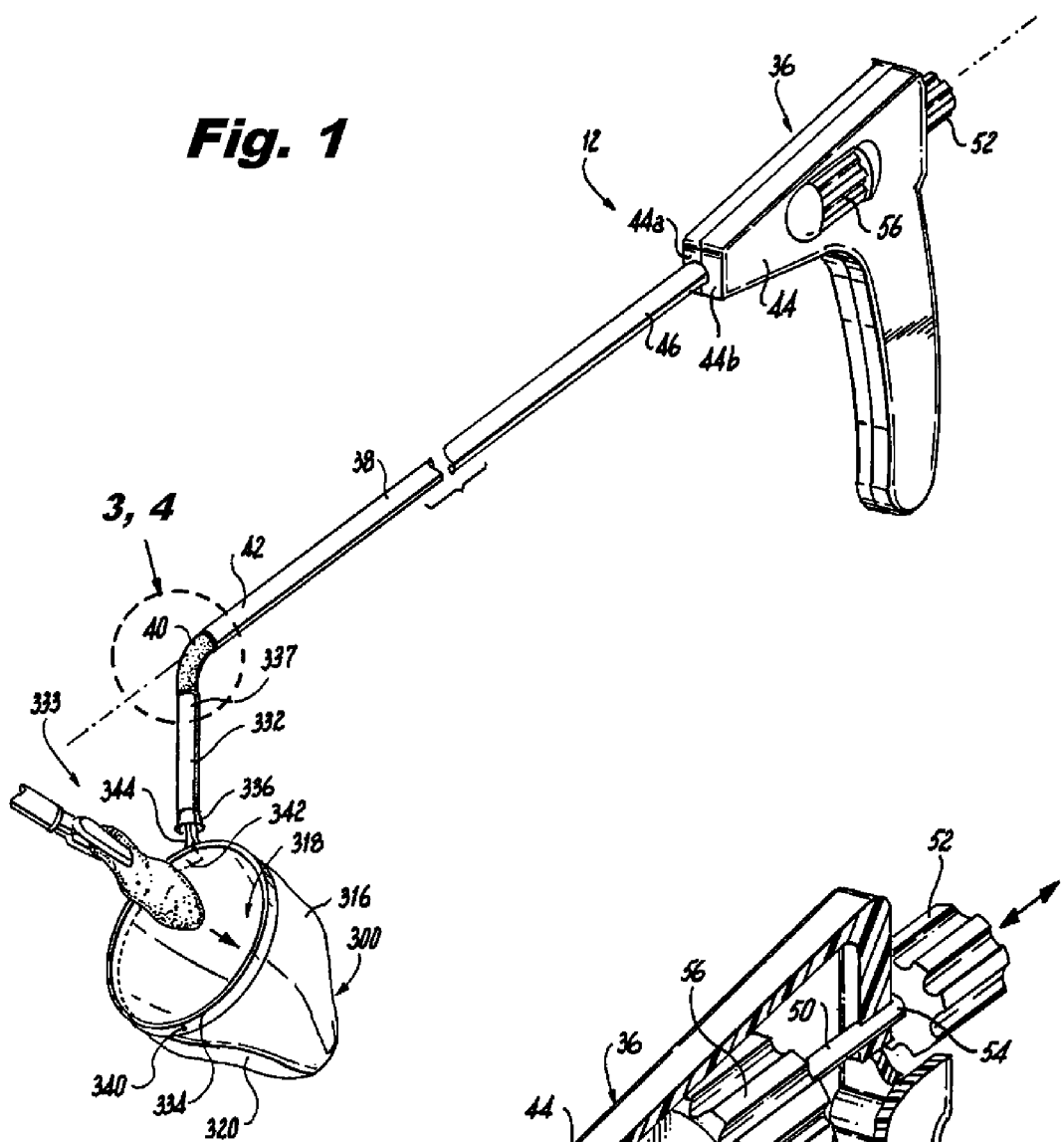
FIG. 1 is a perspective view of one embodiment of a surgical retrieval apparatus provided in accordance with the present disclosure.

Various embodiments of the presently disclosed surgical retrieval apparatus, and methods of making and using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Referring initially to FIG. 1, one embodiment of a surgical retrieval apparatus is shown generally including a specimen retrieval device 330 and a handpiece 12. Specimen retrieval device 330 generally includes an end effector assembly 333 having a multi-chamber collection bag 300 coupled thereto. End effector assembly 333 defines a generally a circular support ring 334 engaged to and extending from a distal end 336 of elongate tubular member 332 (although end effector assembly 333 may alternatively be deployable from elongated tubular member 332), and a semi-circular flip ring 338 (FIGS. 7-9) pivotably coupled to circular support ring 334. As will be described in greater detail below, end effector assembly 333 is configured to retain multi-chamber collection bag 300 thereon and to selectively provide access to first chamber 318 and second chamber 322 (FIG. 9) of first and second packets 316, 320, respectively, of collection bag 300, depending on the position of flip ring 338 (FIGS. 7-9) relative to circular support ring 334.

Figure 2:
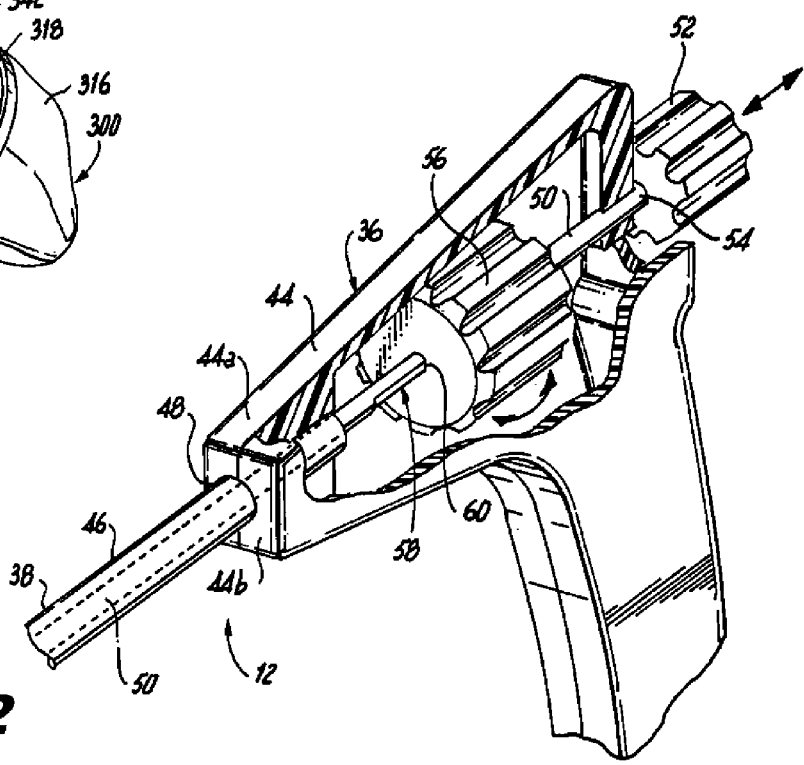
FIG. 2 is a perspective, cut-away view of a handle portion of the surgical retrieval apparatus of FIG. 1.

The handpiece 12 of the surgical retrieval apparatus, as shown in FIGS. 1 and 2, generally includes a handle portion 36 and an elongate tubular member 38 extending distally from handle portion 36. Specimen retrieval device 330 is connected to an articulating portion 40 of handpiece 12 that extends from a distal end 42 of elongate tubular member 38. Articulating portion 40 is provided to allow specimen retrieval device 330 to initially lie substantially parallel to elongate tubular member 38 for ease of insertion and removal through an access port in tissue (not shown). Articulating portion 40 is articulatable from this initial position to an articulated position to move the specimen retrieval device 330 to angular positions with respect to the longitudinal axis of the elongate tubular member 38 to facilitate receipt of a tissue specimen (or tissue specimens) within collection bag 300.

Handle portion 36 of handpiece 12 includes a housing 44 having housing halves 44a and 44b. A proximal end 46 of elongate tubular member 38 is affixed to housing halves 44a and 44b and extends through a distal opening 48 in housing 44. As best shown in FIG. 2, handpiece 12 includes a central rod 50 which extends through housing 44 and through elongate tubular member 38 and into housing 44. Central rod 50 is selectively translatable to move articulating portion(s) 40 to the articulated position, and is also selectively rotatable to rotate flip ring 338 (FIGS. 7-9) to provide access to either first chamber 318 of first packet 316 or second chamber 322 of second packet 320 (see FIGS. 5-11) of collection bag 300. Proximal end 54 of central rod 50 extends proximally through housing 44, ultimately engaging an articulation knob 52. Articulation knob 52 is selectively translatable relative to housing 44 to translate central rod 50 longitudinally within elongate tubular member 38 in order to articulate specimen retrieval device 330 relative to elongate tubular member 38, as will be described in greater detail hereinbelow.

With continued reference to FIGS. 1 and 2, a rotation knob 56 is provided to permit selective rotation of central rod 50 of specimen retrieval device 330. Rotation knob 56 is rotatably mounted within housing 44 and is mounted about a keyed section 58 of central rod 50. Keyed section 58 extends through a keyway 60 in rotation knob 56 which allows central rod 50 to move longitudinally through rotation knob 56 to actuate articulating portion 40 while at the same time being rotatable by rotation knob 56 to correspondingly rotate central rod 50 of specimen retrieval device 330. In other words, although central rod 50 is selectively translatable relative to rotation knob 56, rotation knob 56 is retained in engagement with central rod 50 via keyed section 58 such that rotation knob 56 may be rotated to rotate flip ring 338 (FIGS. 7-9) of end effector assembly 333.

Figure 3:
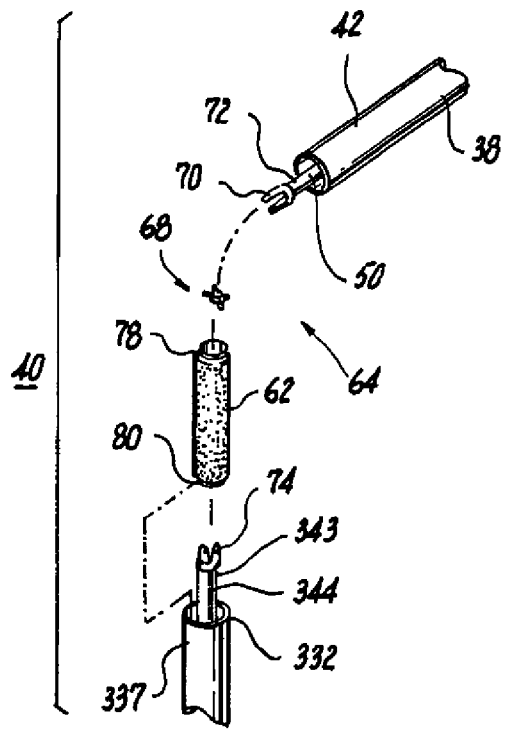
FIG. 3 is a perspective view of the area of detail indicated in FIG. 1, shown with parts separated.
Figure 4:
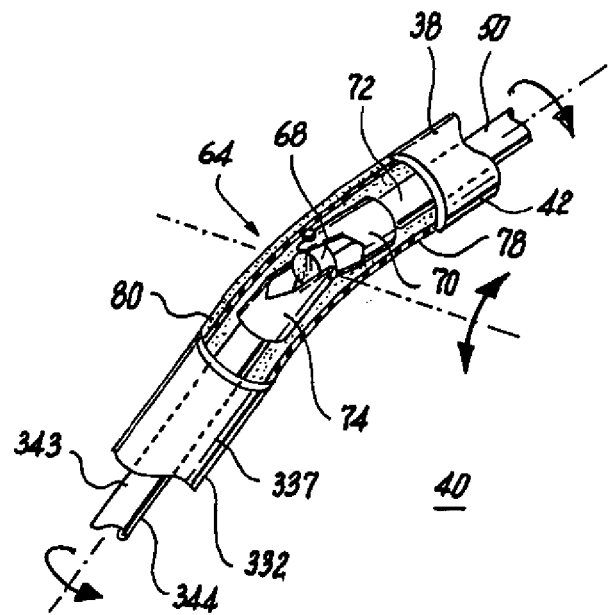
FIG. 4 is an enlarged, perspective, cut-away view of the area of detail indicated in FIG. 1.

Referring now to FIGS. 3 and 4, in conjunction with FIGS. 1 and 2, articulating portion 40 generally includes a flexible articulation tube 62 and an articulation mechanism 64 positioned within flexible articulation tube 62. Flexible articulation tube 62 can be formed from a variety of flexible, biocompatible materials, such as, for example polymers, rubbers, silicones, etc. Articulation mechanism 64 is a U-joint type and generally includes a central member 68 and a first clevis 70 affixed to a distal end 72 of central rod 50. Articulation mechanism 64 additionally includes a second clevis 74 affixed to a proximal end 343 of rotatable center rod 344 of specimen retrieval device 330. Central member 68 pivotably interconnects first clevis 70 and second clevis 74 to permit articulation of specimen retrieval device 330 relative to elongate tubular member 38 of handpiece 12. A proximal end 78 of flexible articulation tube 62 is affixed to distal end 42 of elongate tubular member 38 and a distal end 80 of flexible articulation tube 62 is affixed to a proximal end 337 of elongate tubular member 332 of specimen retrieval device 330. Articulation mechanism 64 is selectively translatable through elongate tubular member 38 and flexible articulation tube 62, e.g., via translation of articulation knob 52, between the unarticulated position, wherein articulation mechanism 64 is disposed within elongated tubular member 38 such that articulation of articulation mechanism 64 is inhibited, and the articulated position, wherein articulation mechanism 64 is disposed within flexible articulation tube 62 such that articulation mechanism 64 is permitted to articulate.

Initially, articulation mechanism 64 is disposed within elongate tubular member 38 such that specimen retrieval device 330 is longitudinally oriented relative to elongate tubular member 38 of handpiece 12. In order to articulate specimen retrieval device 330, central rod 50 is translated distally, e.g., via distal translation of articulation knob 52, through elongate tubular member 38 such that articulation mechanism 64 is disposed within flexible articulation tube 62, thereby permitting second clevis 74 to pivot relative to first clevis 70 to articulate the specimen retrieval device. It should be noted that while articulation mechanism 64 is disclosed as a U-joint mechanism other known articulation mechanisms of the type used in surgical instruments are contemplated herein.

Figure 5:
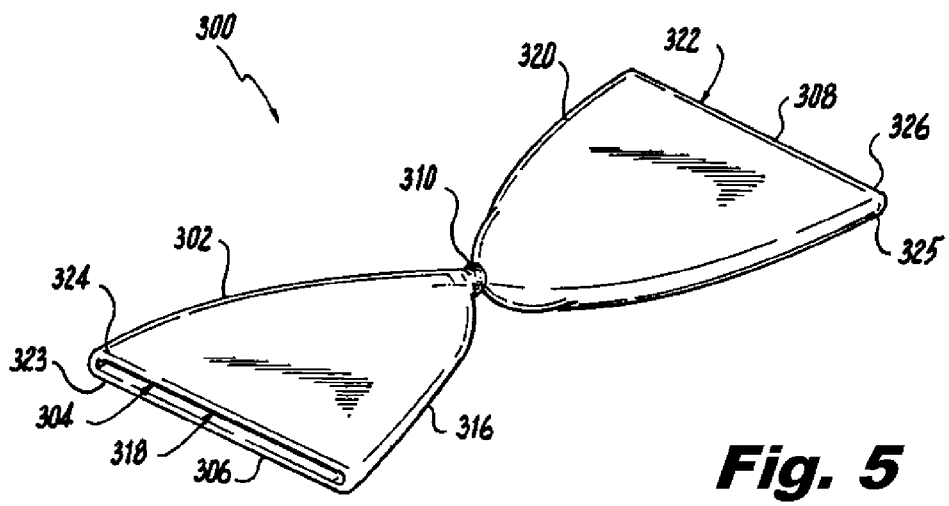
FIG. 5 is a perspective view of a multi-chamber collection bag configured for use with the surgical retrieval apparatus of FIG. 1, shown in an unfolded condition.

Referring now to FIGS. 5-11, and initially to FIG. 5, there is disclosed a multi-chamber collection bag 300 for receipt of multiple tissue specimens. Although multi-chamber collection bag 300 is shown as a dual-chamber collection bag, it is envisioned that greater than two chambers may also be provided. Dual chamber collection bag 300 is formed from a sleeve of material 302 defining a hollow interior 304. During manufacturing, as can be appreciated, a plurality of sleeves of material 302 may be cut from a single elongated sleeve (not shown) of material for making multiple collection bags 300, thus obviating the need to form the material for each bag separately. Alternatively, the bags can be formed of separate materials.

Figure 9:
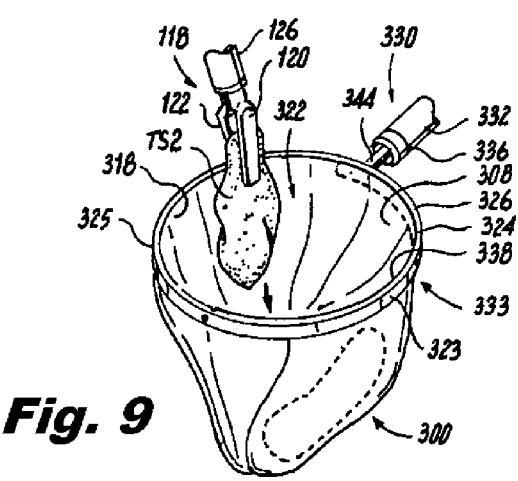
FIG. 9 is a perspective view of the surgical retrieval apparatus of FIG. 7 illustrating insertion of a second tissue specimen into a second chamber of the multi-chamber collection bag.

Sleeve of material 302 has a first open end 306 and a second open end 308. In order to form multiple chambers within sleeve of material 302, a central constriction or divider, e.g., a weld 310, is formed intermediate first open end 306 and second open end 308. Weld 310 divides sleeve of material 302 to form a first packet 316 defining a first chamber 318 for receipt of a first tissue specimen "TS1" (FIG. 7) and a second packet 320 having a second chamber 322 for receipt of a second tissue specimen "TS2" (FIG. 9). Depending on a particular purpose, packets 316, 320 may define similar or different sizes, e.g., weld 310 may be formed closer to first open end 306, closer to second open end 308, or may be located centrally therebetween. Weld 310 is formed by using a radio frequency (RF) welding technique, or any other suitable welding technique. Alternatively, the divider separating first and second packets 316 and 320, respectively, may be formed by any other suitable process, e.g., shrink wrapping sleeve of material 302, applying internal glue within sleeve of material 302, heat shrinking, etc.

Figure 6:
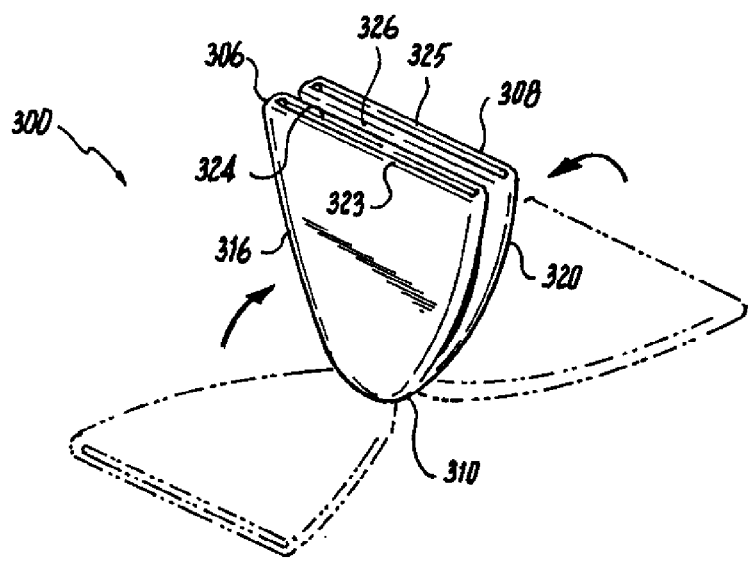
FIG. 6 is a perspective view of the multi-chamber collection bag of FIG. 5 being folded during assembly.

With reference to FIG. 6, in order to prepare dual chamber collection bag 300 for use in a specimen retrieval instrument, as will be described in greater detail hereinbelow, first and second packets 316 and 320 are folded together about central weld 310 such that respective first and second open ends 306, 308 are brought together in abutting relationship. Thereafter, first and second inner portions 324 and 326 are secured to one another utilizing known methods such as, for example, gluing, welding, etc. By securing first and second inner portions 324 and 326 to one another such that first and second packs 316, 320 share a common inner wall, first and second packets 316 and 320 can alternately be opened and closed by moving the joined portions 324, 326 back and forth, e.g., between a position adjacent outer portion 323 of first packet 316 (wherein first packet 316 is closed and second packet 320 is open) and a position adjacent outer portion 325 of second packet 320 (wherein second packet 320 is closed and first packet 316 is open).

Referring now to FIGS. 7-11, in conjunction with FIGS. 1-2, once first and second packets 316 and 320 of dual chamber collection bag 300 have been assembled, dual chamber collection bag 300 is then engaged to specimen retrieval device 330. Specimen retrieval device 330 generally includes an elongate tubular member 332 having an end effector assembly 333 disposed at distal end 336 thereof. Elongate tubular member 332 is coupled to elongate tubular member 38 of handpiece 12 via flexible articulation tube 62 of articulation mechanism 64 to permit articulation of specimen retrieval device 330 relative to handpiece 12. End effector assembly 333, as mentioned above, includes a circular support ring 334 engaged to and extending from distal end 336 of elongate tubular member 332, and a central flip ring 338 having a distal end 340 pivotally engaged to circular support ring 334 and a proximal end 342 engaged to rotatable center rod 344 of specimen retrieval device 330, which extends through elongate tubular member 332, ultimately coupling to central rod 50 of handpiece 12. Thus, rotation of central rod 50, e.g., via rotation of rotation knob 56, effects similar rotation of rotatable center rod 344 within elongate tubular member 332 to pivot central flip ring 338 within circular support ring 334 from a first position, wherein first chamber 318 of first packet 316 of collection bag 300 is accessible for depositing a tissue specimen therein, and a second position, wherein second chamber 322 of second packet 320 of collection bag 300 is accessible for depositing a tissue specimen therein.

Dual-chamber collection bag 300 is attached to specimen retrieval device 330 by attaching the outer portions 323, 325 of first and second open upper ends 306, 308 of first and second packets 316, 320, respectively, to circular support ring 334. The joined inner portions 324, 326 of first and second open upper ends 306, 308 of first and second packets 316, 320, respectively, are attached to flip ring 338. Thus, rotation of flip ring 338 within circular support ring 334 functions to alternately open and close first and second packets 316 and 320. Upper ends 306, 308 of first and second packets 316, 320, respectively, of collection bag 300 may be attached to circular support ring 334 and flip ring 338 in any suitable fashion, e.g., upper ends 306, 308 of first and second packets 316, 320, respectively, may be looped about circular support ring 334 and flip ring 338.

Figure 7:
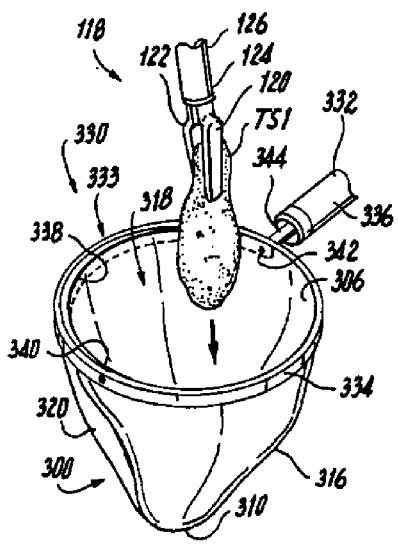
FIG. 7 is a perspective view of the surgical retrieval apparatus of FIG. 1 incorporating the multi-chamber collection bag of FIG. 5, during initial insertion of a tissue specimen.

In use, with continued reference to FIGS. 7-11, in conjunction with FIGS. 1-2, specimen retrieval device 330, including dual chamber collection bag 300, is inserted into the body cavity of a patient (not shown), is articulated into position, e.g., via translation of articulation knob 52 from the unarticulated position to the articulated position, and is prepared for receiving a tissue specimen by rotating or flipping flip ring 338, as shown in FIG. 7, to the first position, e.g., via rotating rotation knob 56 in a first direction, such that first chamber 318 of first packet 316 of collection bag 300 is accessible for depositing a tissue specimen therein. A grasping instrument such as, for example, grasper 118 having first and second movable jaws 120 and 122 (or any other suitable grasping instrument), is used to grasp a first tissue specimen "TS1" and deposit first tissue specimen "TS1" through first open end 306 and into first chamber 318 of first packet 316.

Figure 8:
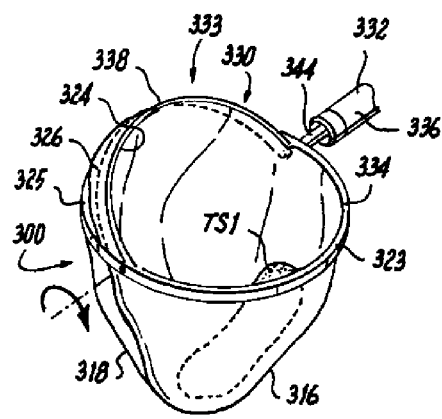
FIG. 8 is a perspective view of the surgical retrieval apparatus of FIG. 7 illustrating switching openings of the multi-chamber collection bag.

Referring now to FIGS. 8-9, in conjunction with FIGS. 1-2, once first tissue specimen "TS1" has been fully received within first packet 316, specimen retrieval device 330 is actuated, e.g., via rotation of rotation knob 56 in a second, opposite direction, to rotate center rod 344 such that flip ring 338 pivots across circular support ring 334 from the first position to the second position, as shown in FIGS. 8-9, such that second chamber 322 of second packet 320 of collection bag 300 is accessible for depositing a tissue specimen therein. More specifically, the rotation of flip ring 338 from the first position to the second position draws the inner portions 324, 326 of first and second packets 316, 320, respectively, across circular support ring 334 to thereby close first open end 306 of first packet 316 and open second open end 308 of second packet 320.

With reference to FIG. 9, a grasper 118 (or other suitable instrument) is utilized to grasp a second tissue specimen "TS2" between jaws 120 and 122 and deposit the tissue specimen "TS2" through second open end 308 and into second chamber 322 of second packet 320. After first and second tissue specimen "TS1" and "TS2" have been deposited into collection bag 300, specimen retrieval device 330 may be used to withdraw collection bag 300 out of the body cavity of a patient.

Figure 10:
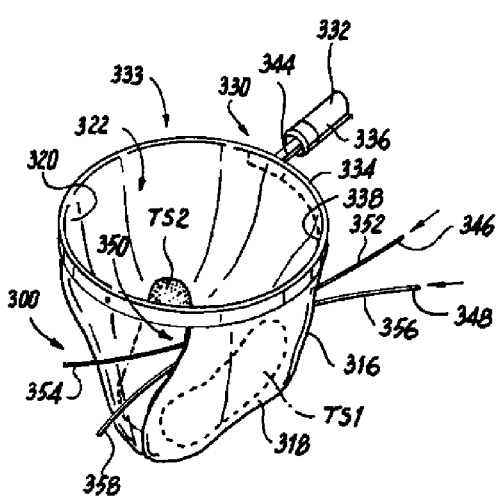
FIG. 10 is a perspective view of the surgical retrieval apparatus of FIG. 7 illustrating the positioning of sutures about the chambers of the multi-chamber collection bag.
Figure 11:
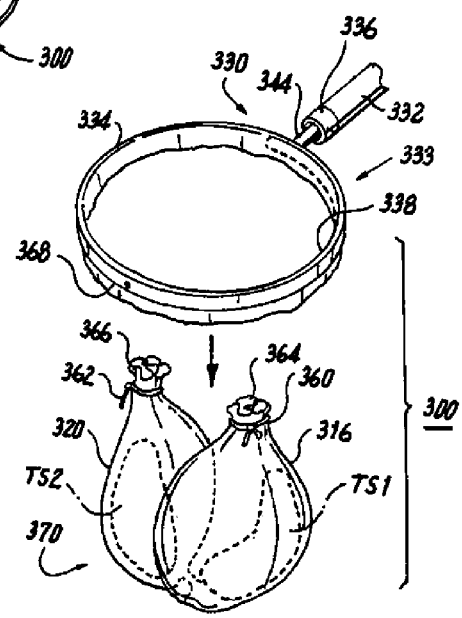
FIG. 11 is a perspective view of the multi-chamber collection bag illustrating the chambers cinched closed about the tissue specimens and the multi-chamber collection bag severed from the specimen retrieval device.

Referring now to FIGS. 10-11, alternatively, or additionally, a pair of first and second sutures 346 and 348 may be inserted through a gap 350 defined between folded first and second packets 316 and 320 to tie off first and second packets 316 and 320 prior to removal from the body cavity. Specifically, first and second ends 352 and 354 of first suture 346 are wrapped around first packet 316 and first and second ends 356 and 358 of second suture 348 are wrapped around second packet 320. First and second ends 352 and 354 of first suture 346 are tied together to form a first cinch 360 and first and second ends 356 and 358 of second suture 348 are tied together to form a second cinch 362 about second packet 320.

Referring now specifically to FIG. 11, after first and second cinches 360 and 362 have been formed to tie off first and second packets 316 and 320, a first upper end 364 of first packet 316 and a second upper end 366 of second packet 320 are severed or cut apart from a remaining or remnant amount of material 368 of sleeve of material 302 that remains affixed to outer support ring 334 and flip ring 338 of specimen retrieval device 330. This forms a double packet bag 370, securely containing first and second tissue specimens "TS1" and "TS2" within first and second respective packets 316 and 320, for ease of removal through a surgical access port or other opening. In this manner, collection bag 300, in conjunction with specimen retrieval device 330, provides a safe and secure method of simultaneously removing multiple tissue sections from within a body cavity.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical retrieval apparatus for receipt of multiple tissue specimens, the surgical retrieval apparatus comprising:
   a collection bag including first and second packets, each packet having an outer portion and an inner portion, the first and second packets defining first and second adjacent chambers, each chamber configured for receipt of a tissue specimen therein;
   a support ring, the first and second packets coupled to the support ring;
   a flip ring pivotably coupled to the support ring, the first and second packets coupled to the flip ring, the flip ring rotatable relative to the support ring between a first position, wherein the first chamber is accessible for depositing a tissue specimen therein, and a second position, wherein the second chamber is accessible for depositing a tissue specimen therein;
   an elongated tubular member coupled to the support ring; and
   a rod extending through the elongated tubular member, the rod coupled to the flip ring and configured to rotate the flip ring between the first and second positions.

2. The surgical retrieval apparatus according to claim 1, wherein when the first chamber is accessible the second chamber is closed, and when the second chamber is accessible the first chamber is closed.

3. The surgical retrieval apparatus according to claim 1, wherein the outer portions of the first and second packets are coupled to the support ring.

4. The surgical retrieval apparatus according to claim 1, wherein the inner portions of the first and second packets are coupled to the flip ring.

5. The surgical retrieval apparatus according to claim 1, wherein the rod is rotatably disposed within the elongated tubular member, and wherein rotation of the rod relative to the elongated tubular member rotates the flip ring between the first and second positions.

6. The surgical retrieval apparatus according to claim 5, further comprising a rotation knob coupled to the flip ring, the rotation knob selectively rotatable to effect corresponding rotation of the rod to rotate the flip ring between the first and second positions.

7. The surgical retrieval apparatus according to claim 1, wherein the elongated tubular member defines a longitudinal axis and wherein the collection bag is articulatable relative to the longitudinal axis.

8. The surgical retrieval apparatus according to claim 7, further comprising an articulation knob, the articulation knob selectively movable to articulate the collection bag.

9. The surgical retrieval apparatus according to claim 1, wherein the inner portions of the first and second packets are attached to one another.

10. The surgical retrieval apparatus according to claim 1, further comprising first and second sutures extending between the first and second packets, the sutures configured to facilitate cinching the first and second packets closed.

11. The surgical retrieval apparatus according to claim 1, wherein the support ring defines a generally circular configuration and the flip ring defines a generally semi-circular configuration.

12. A surgical retrieval apparatus, comprising:
 a handle portion;
 an elongated tubular member;
 a collection bag positioned distal of the elongated tubular member and including first and second packets, the first packet defining a first chamber with a first opening and the second packet defining a second chamber with a second opening;
 a flip ring operably coupled to the collection bag to and movable between first and second positions to alternatingly expose the first and second openings of the first and second packets, respectively; and
 a rod extending through the elongated tubular member, the rod coupled to the flip ring and configured to move the flip ring between the first and second positions.

13. The surgical retrieval apparatus according to claim 12, further comprising a first suture positioned about an open end of the first packet to cinch the first packet closed to retain a first specimen of tissue therein.

14. The surgical retrieval apparatus according to claim 13, further comprising a second suture positioned about an open end of the second packet to cinch the second packet closed to retain a second specimen of tissue therein.

15. The surgical retrieval apparatus according to claim 12, wherein the first and second packets are releasable from the flip ring.

16. The surgical retrieval apparatus according to claim 12, further comprising a rotation knob, wherein the flip ring is rotated via rotation of a rotation knob to alternatingly expose the first and second openings.

* * * * *